US007049266B2

(12) United States Patent
Choudary et al.

(10) Patent No.: US 7,049,266 B2
(45) Date of Patent: May 23, 2006

(54) LAYERED DOUBLE HYDROXIDES SUPPORTED NANOPALLADIUM CATALYSTS FOR HECK-, SUZUKI, SONOGASHIRA-, AND STILLE TYPE COUPLING REACTIONS OF HALOARENES

(75) Inventors: Boyapati Manoranjan Choudary, Hydrabad (IN); Madhi Sateesh, Warangal (IN); Naidu Sreenivasa Chowdari, Nellore (IN); Mannepalli Lakshmi Kantam, Hydrabad (IN); Bojja Sreedhar, Hydrabad (IN)

(73) Assignee: Indian Institute of Chemical Technology, Andhra Pradesk (IN)

( * ) Notice: Subject to any disclaimer, the term of this patent is extended or adjusted under 35 U.S.C. 154(b) by 0 days.

(21) Appl. No.: 10/403,799

(22) Filed: Mar. 31, 2003

(65) Prior Publication Data

US 2004/0192542 A1    Sep. 30, 2004

(51) Int. Cl.
*B01J 23/44* (2006.01)
*B01J 31/00* (2006.01)
*B01J 27/13* (2006.01)
*B01J 21/08* (2006.01)
*B01J 21/12* (2006.01)

(52) U.S. Cl. ............... 502/339; 502/159; 502/162; 502/164; 502/169; 502/230; 502/262

(58) Field of Classification Search ............ 502/262, 502/339, 159, 162, 164, 169, 230
See application file for complete search history.

(56) References Cited

U.S. PATENT DOCUMENTS

| 5,232,887 | A  | * | 8/1993  | Arena et al. ............ 502/163 |
| 5,286,372 | A  | * | 2/1994  | Arena et al. ............ 208/207 |
| 5,318,936 | A  | * | 6/1994  | Ferm et al. ............. 502/163 |
| 6,074,979 | A  | * | 6/2000  | Hagemeyer et al. ...... 502/159 |
| 6,303,537 | B1 | * | 10/2001 | Wang et al. ............ 502/330 |
| 6,670,515 | B1 | * | 12/2003 | Dubois et al. ........... 585/269 |
| 6,676,919 | B1 | * | 1/2004  | Fischer et al. .......... 423/584 |
| 6,686,310 | B1 | * | 2/2004  | Kourtakis et al. ........ 502/325 |
| 6,706,902 | B1 | * | 3/2004  | Sturmann et al. ........ 549/523 |
| 2002/0009414 | A1 | * | 1/2002 | Moser et al. ............ 502/324 |

FOREIGN PATENT DOCUMENTS

DE            197 12 388            10/1998

OTHER PUBLICATIONS

Ben-David, Y., et al., "Palladium-catalyzed Vinylation of Aryl Chlorides. Chelate Effect in Catalysis" *Organometallics*; 1992; 11(6); pp. 1995-1996.
Reetz, Manfred T., et al., "A New Catalyst System for the Heck Reaction of Unreactive Aryl Halides" *Angewandte Chemie International Edition*; 1998; 37(4); pp. 481-483.
Kostas, I. D., et al., Intraannular Functionalization of the 1,3-Phenylene- 19-Crown-6 System Via Bromine-Lithium Exchange; *Journal of Organometallic Chemistry*; 1998; 572(1); pp. 93-104.
Herrmann, W. A., et al., "Metal Complexes of N-Heterocyclic Carbenes—A New Structural Principle for Catalysts in Homogeneous Catalysis" *Angewandte Chemie International Edition Engl.*; 1995; 34(21); pp. 2371-2374.
Herrmann, W. A., et al., "Application of Palladacycles in Heck Type Reactions" *Journal of Organometallic Chemistry*; 1999; 576(1-2); pp. 23-41.
Portnoy, Moshe, et al., "Clarification of a Remarkable Chelate Effect Leads to Palladium-Catalyzed Base-Free Olefin Arylation" *Organometallics*; 1993; 12(12); pp. 4734-4735.
Littke, A. F., et al., "Heck Reactions in the Presence of $P(t-Bu)_3$: Expanded Scope and Milder Reaction Conditions for the Coupling of Aryl Chlorides" *Journal of Organic Chemistry*; 1999; 64(1); pp. 10-11.
Littke, A. F., et al., "A Versatile Catalyst for Heck Reactions of Aryl Chlorides and Aryl Bromides Under Mild Conditions" *Journal of the American Chemical Society*; 2001; 123(29); pp. 6989-7000.
Ehrentraut, Andreas, et al., "A New Efficient Palladium Catalyst for Heck Reactions of Deactivated Aryl Chlorides" *Synlett*; 2000; 11; pp. 1589-1592.
Shaughnessy, K. H., "A Fluorescence-Based Assay for High-Throughput Screening of Coupling Reactions. Application to Heck Chemistry" *Journal of the American Chemical Society*; 1999; 121(10); pp. 2123-2132.
Böhm, Volker P. W., et al. "Coordination Chemistry and Mechanisms of Metal-Catalyzed C—C Coupling Reactions, Part 12.—Nonaqueous Ionic Liquids: Superior Reaction Media for the Catalytic Heck-Vinylation of Chloroarenes" *Chemistry—A European Journal*; 2000; 6(6); pp. 1017-1025.

(Continued)

*Primary Examiner*—J. A. Lorengo
*Assistant Examiner*—J. Pasterczyk
(74) *Attorney, Agent, or Firm*—Meyerston, Hood, Kivlin, Kowert & Goetzel, P.C.; Eric B. Metertons

(57) ABSTRACT

Processes for the preparation of nanopalladium (0) catalysts are disclosed. In some embodiments, the nanopalladium (0) catalysts may be reusable. In some embodiments, the nanopalladium (0) catalysts may be heterogeneous. Nanopalladium (0) catalysts may be employed for preparing coupling products by C—C bond formation through reaction of haloarenes in the presence of base. Haloarenes used in the coupling reaction may include chloroarenes that are typically unreactive. The use of heterogeneous nanopalladium catalyst may preclude the presence of trace amounts of palladium in the final coupling product.

7 Claims, No Drawings

OTHER PUBLICATIONS

Old, D. W., et al., "A Highly Active Catalyst for Palladium-Catalyzed Cross-Coupling Reactions: Room-Temperature Suzuki Couplings and Amination of Unactivated Aryl Chlorides" *Journal of the American Chemical Society*; 1998; 120(37); pp. 9722-9723.

Littke, Adam F., et al., "A Convenient and General Method for Pd-Catalyzed Suzuki Cross-Couplings of Aryl Chlorides and Arylboronic Acids" *Angewandte Chemie International Edition*; 1998, 37, 3387.

Herrmann, W. A., et al. "Chelating N-Heterocyclic Carbene Ligands in Palladium-Catalyzed Heck-Type Reactions" *Journal of Organometallic Chemistry*; 1998; 557(1); pp. 93-96.

Buchmeiser, Michael R., et al., "Bis(Pyrimidine)-Based Palladium Catalysts: Synthesis, X-ray Structure and Applications in Heck-, Suzuki-, Sonogashira-Hagihara Couplings and Amination Reactions" *Journal of Organometallic Chemistry*; 2001; 634(1); pp. 39-46.

Murata, Miki, et al., "Palladium-Catalyzed Cross-Coupling Reaction of Tributyltin Hydride with Aryl Iodides: Formation of A Tin-Carbon Bond" *Synlett*; 2000; pp. 1043-1045.

* cited by examiner

LAYERED DOUBLE HYDROXIDES SUPPORTED NANOPALLADIUM CATALYSTS FOR HECK-, SUZUKI, SONOGASHIRA-, AND STILLE TYPE COUPLING REACTIONS OF HALOARENES

The present invention relates to a process for the preparation of a reusable heterogeneous nanopalladium(0) catalysts on the solid support to perform C—C bond formation reactions such as Heck, Suzuki, Sonagashira, and Stille type reactions of haloarenes that include unreactive chloroarenes. Layered double hydroxides and Merrifield resin supported nanopalladium catalysts are prepared by an exchange of $PdCl_4^{2-}$ followed by reduction and well characterized for the first time.

This invention particularly relates to an cco-friendly process employing re-usable heterogeneous catalyst in place of soluble palladium catalysts for preparing coupling products by C—C bond formation reaction of haloarenes that include unreactive chloroarenes in the presence of base. The ligand force heterogeneous layered double hydroxides supported nanopalladium (LDH-$Pd^0$) catalyst using the basic LDH in place of basic ligands indeed exhibits higher activity and selectivity in the C—C coupling reactions of haloarenes that include electron poor and electron rich chloroarenes in nonaqueous ionic liquids (NAIL) over the homogeneous $PdCl_2$ system. The coupling products find good applications as intermediates in the preparation of materials, natural products, and bioactive compounds.

There are serious disadvantages in performing the catalytic C—C bond formation reaction with iodoarenes and bromoarenes in the manufacture of olefins due to high cost of the starting materials. Despite the synthetic elegance and high turnover number, these coupling reactions suffer from serious limitations of using the expensive bromo and iodoarenes that precluded the wide use in industry. By employing the heterogeneous catalytic system and chloroarenes as starting materials, the cost naturally comes down due to easy recovery of the catalyst and low cost of chloroarenes when compared with bromo and iodoarenes.

References may be made to the publications, *Organometallics* 1992, 11, 1995, *Angew. Chem. Int. Ed.* 1998, 37, 481, *J. Organomet. Chem.* 1998, 572, 93, *Angew. Chem. Int. Ed. Engl.* 1995, 34, 2371, *J. Organomet. Chem.* 1999, 576, 23 wherein Heck-olefination of chloroarenes is carried by palladium complexes under homogeneous conditions. The inherent disadvantages are difficulty in the recovery of palladium and usage of activated electron poor and nonactivated electron neutral chloroarenes.

References may be made to the publications *Organometallics* 1993, 12, 4734, *J. Org. Chem.* 1999, 64, 10, *J. Am. Chem. Soc*, 2001, 123,6989, *Synlett*, 2000, 11, 1589, *J. Am. Chem. Soc.* 1999, 121, 2123 wherein olefins are prepared from deactivated highly electron rich chloroarenes by palladium complexes. The inherent disadvantage is the usage of expensive sterically hindered phosphine palladium complexes.

Reference may be made to the publication *Chem. Eur. J.*. 2000, 6, 1017 wherein Heck-olefination of deactivated highly electron rich chloroarenes is carried by palladacycle catalysts in the presence of nonaqucous liquids. The inherent disadvantages are the usage of additives and low yields.

Reference may be made to European patent DE-A 197 12 388.0,1997 wherein Heck-olefination of chloroarenes is carried by palladacycle catalyst using an additive. The inherent disadvantage is that no reaction occurs in the absence of phosphonium salt.

Reference may be made to the publications *J. Am. Chem. Soc.*, 1998, 120, 9722 and *Angew. Chem. Int. Ed, Engl.*, 1998, 37, 3387 wherein biphenyls are prepared using arylchlorides with palladium catalysts. The inherent disadvantage is the usage of expensive, air-sensitive phosphine ligands.

Reference may be made to a publication *J. Organometallic Chem.*, 1998, 557, 93 wherein biphenyls are prepared using carbene ancillary ligands with aryl bromides and activated aryl chlorides with palladium catalyst. The drawbacks are longer reaction times and yield from the aryl chloride was relatively low.

Reference may be made to a publication *J. Organomet. Chem.* 2001, 634, 39 wherein diarylacetylenes are prepared using heterogeneous polymer anchored bis(pyrimidine)-based palladium catalyst with chlorobenzene with impressive turnover frequency. The drawback is that it was not tried for electron rich chloroarenes.

Reference may be made to the publication *Synlett*, 2000, 1043 wherein arylstannanes were prepared using palladium catalyst in the presence of potassium acetate. The drawback is that the usage of aryl iodides as substrates.

OBJECTS OF THE INVENTION

The main object of the present invention, is a process for the preparation of a ligand free reusable heterogeneous nanopalladium(0) catalysts by an exchange of $PdCl_4^{2-}$ followed by reduction on the support selected from LDH and S'—$NR_3X$ wherein S' is a unmodified surface support selected from resin and silica, R is an alkyl group selected from the group consisting of methyl, ethyl, propyl, butyl , X is selected from the group consisting of Cl, Br, I, F, OH and OAc to perform C—C bond coupling reactions such as Heck, Suzuki, Sonagashira, and Stille type reactions with haloarenes that include unreactive chloroarenes under standard thermal and microwave conditions using solvents selected from nonaqueous ionic liquid, THF, dioxane, water, NMP at temperature ranging between 20 to 150° C. for a period ranging from 0.5 to 48 h under nitrogen atmosphere and obtaining the desired product by conventional method which obviates the drawbacks as detailed above.

Another object of the present invention is LDH as synthesised having interstitial anions such as chloride, nitrate, carbonate, sulfate or calcination of LDH having the said interstitial anions at temperatures in the range of 350 to 550 C are used as precursors for the preparation of LDH-Pd(0) catalysts.

Another object of the present invention is to reduce the reaction time by employing microwave irradiation. Using microwave irradiation, the rate of C—C coupling reaction is accelerated manifold with the highest turnover frequency ever recorded both in the case of electron poor and electron rich chloroarenes.

Still another object of the present invention is the quantity of nanopalladium catalyst used in the reaction is 0.1 to 3 mol % of palladium with respect to the substrate.

Yet another object of the present invention is to recover the heterogeneous palladium catalyst used in the C—C coupling reactions such as Heck, Suzuki, Sonagashira, and Stille type reactions by simple filtration and reuse for number of cycles with consistent activity.

SUMMARY OF THE INVENTION

The novelty of the present invention, is a process for the preparation of a ligand free reusable heterogeneous nanopalladium(0) catalysts by an exchange of $PdCl_4^{2-}$ followed by reduction on the support selected from LDH and S'—$NR_3X$ wherein S' is a unmodified surface support selected from resin and silica, R is an alkyl group selected from the group consisting of methyl, ethyl, propyl, butyl, X is selected front the group consisting of Cl, Br, I, F, OH and OAc to perform C—C bond coupling reactions such as Heck, Suzuki, Sonagashira, and Stille type reactions with haloarenes that include unreactive chloroarenes under standard thermal and microwave conditions using solvents selected from nonaqucous ionic liquid, THF, dioxane, water, NMP at temperature ranging between 20 to 150° C. for a period ranging from 0.5 to 48 h under nitrogen atmosphere and obtaining the desired product by conventional method.

In an embodiment of the present invention, the quantity of nanopalladium(0) catalyst used in the reaction is 0.1 to 3 mol % of palladium with respect to the substrate.

In an embodiment of the present invention, nanopalladium (0) catalysts are recovered by simple filtration and reused for several cycles with consistent activity.

In another embodiment of the present invention, the solvents selected for the C—C bond formation reactions are nonaqueous liquid, water, 1,4-dioxane, THF, NMP.

In yet another embodiment of the present invention, the base used is selected from the known group consisting of triethylamine, tributylamine, potassium fluoride, potassium acetate.

In still another embodiment of the present invention, the reactions are preferably, effected at a known temperature in the range of 20 to 150° C. for a period 0.5 to 48 h.

In still another embodiment of the present invention, is to reduce the reaction time by employing microwave irradiation. Using microwave irradiation, the rate of C—C coupling reaction is accelerated manifold with the highest turnover frequency ever recorded both in the case of electron poor and electron rich chloroarenes.

In yet another embodiment of the present invention, a phosphine free new recyclable heterogeneous catalytic system was developed to dispense the use of expensive and air sensitive basic phosphincs for palladium catalyzed coupling reactions of chloroarenes. The basic support, Mg—Al layered double hydroxides (LDH) selected not only stabilizes the nanopalladium particles but also provides the adequate electron density to the anchored $Pd^0$ species to facilitate oxidative addition of even the deactivated electron rich chloroarenes.

DETAILED DESCRIPTION OF THE INVENTION

Heterogeneous nanopalladium(0) catalysts are prepared by an exchange of $PdCl_4^{2-}$ on the support selected from LDH and S'—$NR_3X$ wherein S' is a unmodified surface support selected from resin and silica, R is an alkyl group selected from the group consisting of methyl, ethyl, propyl, butyl, X is selected from the group consisting of Cl, Br, I, F, OH and OAc in an aqueous solvent at a temperature ranging between 20 to 30° C. for a period ranging from 5 to 24 h under nitrogen atmosphere followed by filtration and reduction with hydrazine hydrate in ethanol at room temperature. Filtration gave the desired nanopalladium(0) catalysts.

C—C bond coupling products are prepared by using the recyclable nanopalladium(0) catalysts by Heck, Suzuki, Sonagashira, and Stille type reactions of haloarenes that include unreactive chloroarenes in a under standard thermal and microwave conditions using solvents selected from nonaqueous ionic liquid, water, THF, dioxan, and NMP at a temperature ranging between 20 to 150° C. for a period 0.5 to 48 h under nitrogen atmosphere, and obtaining the pure C—C coupling products by a conventional method.

The palladium content in the catalyst ranges between 0.1 to 3 mol % with respect to the substrate. Nanopalladium (0) catalysts are recovered by simple filtration and reused for several cycles with consistent activity.

The solvents selected for the C—C bond formation reaction is selected from the group consisting of nonaqueous ionic liquid, water, 1,4-dioxane, THF, NMP or any mixture thereof. The base used is selected from the group consisting of triethylamine, tributylamine, potassium fluoride, potassium acetate.

Scientific Explanation:

In the present invention, we synthesized LDH, silica, resin supported nanopalladium catalysts for the first time and used in catalytic amounts for preparing coupling products by C—C bond formation reactions involving Heck-, Suzuki-, Sonagashira- and Stille type coupling of haloarenes that include chloroarenes in presence of base.

Heterogeneous nanopalladium(0) catalysts are prepared by an exchange of $PdCl_4^{2-}$ followed by reduction on silica or resin or LDH.

The nanopalladium (0) on supports is responsible for the activity of catalyst in C—C coupling reactions. The activity of heterogeneous nanopalladium catalysts is similar or higher than the homogeneous counter parts. The basic support, Mg—Al layered double hydroxides (LDH) is selected as the material of choice, which not only stabilizes the nanopalladium particles but also provides the adequate electron density to the anchored $Pd^0$ species to facilitate oxidative addition of even the deactivated electron rich chloroarenes.

Higher yields and stereoselectivities are obtained when nanopalladium catalysts are used. Incidentally this forms the first report of heterogeneous palladium catalyst employed in the Stille type coupling. The consistent activity obtained for several cycles makes the process economical and possible for commercial realization.

The coupling products find good applications as intermediates in the preparation of materials, natural products, and bioactive compounds. Thus this invention offers the best techno-economic route for the synthesis of coupling products. Therefore, nanopalladium catalysts are better option for the C—C bond formation reaction of haloarenes that include chloroarenes.

Nanopalladium catalysts are prepared as exemplified and used in catalytic amounts for preparing coupling products by C—C bond formation reaction in presence of base in a heterogeneous way as described in the examples.

The following examples are given by way of illustration of the present invention and therefore should not be construed to limit the scope of the invention.

Preparation of Nanopalladium Catalysts

EXAMPLE 1

Preparation of LDH (Mg—Al—Cl) (1)

A mixture of $MgCl_2.6H_2O$ (30.49 g, 0.15 mmol) and $AlCl_3.6H_2O$ (12.07 g, 0.05 mmol) was dissolved in 200 ml of deionised water. To this aqueous solution, 100 ml of NaOH (2M) solution was slowly added at 25° C. and a further amount of 2M NaOH solution was added to maintain a pH of 10 under nitrogen flow. The resulting suspension was stirred overnight at 70° C. The solid product was isolated by filtration, washed thoroughly with deionised water and dried overnight at 80° C. All the synthetic steps were carried out using decarbonated water.

EXAMPLE 2

Preparation of $Na_2PdCl_4$ (2)

$Na_2PdCl_4$ was prepared by refluxing $PdCl_2$ (1.77 g, 10 mmol) and sodium chloride (0.58 g, 10 mmol) in 50 mL for 4 h. The solution was filtered in hot condition to avoid NaCl contamination. Evaporation of the filtrate gave dark brown flakes (2.88 g, 98%).

EXAMPLE 3

Preparation of $LDH-PdCl_4$ (3)

Mg—Al—Cl (1.5 g) was suspended in 150 mL of aqueous $Na_2PdCl4$ (0.441 g, 1.5 mmol) solution and stirred at 25° C. for 12 h under nitrogen atmosphere. The solid catalyst was filtered, washed thoroughly with 500 mL of water and vacuum-dried to obtain 1.752 g of $LDH-PdCl_4$ (0.86 mmol of Pd per gram).

EXAMPLE 4

Preparation of $LDH-Pd^0$ (4)

$LDH-PdCl_4$ (1 g) was reduced with hydrazine hydrate (1 g, 20 mmol) in ethanol (10 mL) for 3 h at room temperature, filtered and washed with ethanol to give an air stable black powder (0.95 mmol of Pd per gram).

EXAMPLE 5

Preparation of $Resin-PdCl_4$ (5)

Resin was obtained by quaternization of triethylamine (2.1 mL, 21 mmol) with one gram of chloromethylated styrene-divinylbenzene copolymer (Merrifield resin, capacity ~2.1 mcquiv/g) in chloroform (20 mL) under reflux for 24 h. Quaternary ammonium resin (1 g) was suspended in 100 mL of (0.294 g, 1 mmol) aqueous $Na_2PdCl_4$ solution and stirred at 25° C. for 12 h under nitrogen atmosphere. The solid catalyst was filtered, washed thoroughly with water (300 mL) and vacuum-dried to obtain $resin-PdCl_4$ (0.8 mmol of Pd per gram).

EXAMPLE 6

Preparation of $Resin-Pd^0$ (6)

$Resin-PdCl_4$ (1 g) was reduced with hydrazine hydrate (1 g, 20 mmol) in ethanol (10 mL) for 3 h at room temperature, filtered and washed with ethanol to give an air stable black beads (0.87 mmol of Pd per gram).

EXAMPLE 7

Preparation of $Silica-PdCl_4$ (7)

Modified silica was obtained by quaternization of triethylamine (0.7 mL, 7 mmol) with bromopropylsilica (capacity 0.7 mcquiv/g) in chloroform (20 mL) under reflux for 24 h. 1 g of quaternary ammonium silica was suspended in 100 mL of 0.33 mmol aqueous $Na_2PdCl_4$ solution and stirred at 25° C. for 12 h under nitrogen atmosphere. The solid catalyst was filtered, washed thoroughly with 300 mL of water and vacuum dried to obtain $SiO_2$—$PdCl_4$.

EXAMPLE 8

Preparation of $Silica-Pd^0$ (8)

$Silica-PdCl_4$ (1 g) was reduced with hydrazine hydrate (1 g, 20 mmol) in ethanol (10 mL) for 3 h at room temperature, filtered and washed with ethanol to give an air stable black powder.

C—C Bond Forming Reactions

The C—C bond forming reactions were performed using $LDH-Pd^0$ catalysts to evaluate nanopalladium catalysts of the present invention.

1. Heck-Olefination

Scheme 1

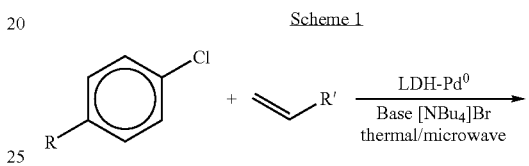

R = H, $OCH_3$, $NO_2$, $CH_3$, etc.
R' = aryl, vinyl
Yield = 80–95% (microwave)
76–98% (thermal)
Time = 0.5–1 h (microwave)
10–40 h (thermal)

EXAMPLE 9

Heck-Olefination Between Chlorobenzene and Styrene Catalysed by $LDH-Pd^0$ Under Thermal Conditions In a 100 mL Schlenk flask, the NAIL (3.23 g, 10 mmol) ($NBu_4Br$) was heated to melt (130° C.) and degassed with nitrogen and vacuum prior to the addition of other reagents. After cooling the NAIL to room temperature, $LDH-Pd^0$ (3 mol %), tri-n-butyl amine (222 mg, 1.2 mmol) were added. The styrene (1.2 mmol) and chlorobenzene (1 mmol) were then added and the reaction was heated to 130° C. and stirred for 10–40 h under nitrogen atmosphere, After completion of the reaction, the $LDH-Pd^0$ catalyst was filtered and washed with water and dichloromethane. After removing the solvent, the crude material was chromatographed on silica gel or recrystallized from ethanol to afford the trans-stilbene.

EXAMPLES 10–17

The procedure was followed as in example 9 with various substrates under thermal conditions and the results are presented in Table 1.

TABLE 1

LDH-Pd⁰ Catalyzed Heck-Olefination of Chloroarenes under thermal conditions[a]

| Example | Chloroarene | Olefin | Time (h) | Yield (%) |
|---|---|---|---|---|
| 9 | C₆H₅–Cl | CH₂=CH–C₆H₅ | 30 | 98 |
| 10 | 4-O₂N-C₆H₄-Cl | CH₂=CH–C₆H₅ | 10 | 95 |
| 11 | 4-MeOC-C₆H₄-Cl | CH₂=CH–C₆H₅ | 15 | 97 |
| 12 | 4-OHC-C₆H₄-Cl | CH₂=CH–C₆H₅ | 15 | 98 |
| 13 | 4-PhOC-C₆H₄-Cl | CH₂=CH–C₆H₅ | 15 | 93 |
| 14 | 4-MeO-C₆H₄-Cl | CH₂=CH–C(O)OnBu | 40 | 86 |
| 15 | 4-MeO-C₆H₄-Cl | CH₂=CH–C₆H₅ | 40 | 76 (5)[b] |
| 16 | 4-Me-C₆H₄-Cl | CH₂=CH–C₆H₅ | 30 | 96 (55)[b] |
| 17 | 4-HOH₂C-C₆H₄-Cl | CH₂=CH–C₆H₅ | 30 | 92 (51)[b] |

[a]Chloroarene (1 mmol), olefin (1.2 mmol) LDH-Pd⁰ (3 mol %), [NBu₄]Br (10 mmol), and tri-n-butyl amine (1.2 mmol). Reactions are conducted at 130° C.
[b]The values in parentheses refer to the homogeneous reaction conducted with PdCl₂ under identical conditions.

EXAMPLE 18

Heck-Olefination Between Chlorobenzene and Styrene Catalysed by LDH-Pd⁰ Under Microwave Conditions.

Styrene (1.2 mmol), chlorobenzene (1 mmol), LDH-Pd⁰ (3 mol %), tri-n-butyl amine (222mg, 1.2 mmol) and NAIL (3.23 g, 10 mmol) were taken in a teflon vessel, closed and irradiated in a Miele Electronic M270 microwave oven at 400W and 130° C. for 0.5–1 h. After completion of the reaction, the LDH-Pd⁰ catalyst was filtered and washed with water and dichloromethane. After removing the solvent, the crude material was chromatographed on silica gel to afford the trans-stilbene.

EXAMPLES 19–26

The procedure was followed as in example 18 with various substrates under microwave conditions and the results are presented in Table 2.

TABLE 2

LDH-Pd⁰ Catalyzed Heck-Olefination of Chloroarenes under microwave conditions[a]

| Example | Chloroarene | Olefin | Time (h) | Yield (%) |
|---|---|---|---|---|
| 18 | chlorobenzene | styrene | 0.5 | 95 |
| 19 | 4-nitrochlorobenzene | styrene | 0.5 | 96 |
| 20 | 4-chloroacetophenone (MeOC-C$_6$H$_4$-Cl) | styrene | 0.5 | 93 |
| 21 | 4-chlorobenzaldehyde (OHC-C$_6$H$_4$-Cl) | styrene | 0.5 | 95 |
| 22 | 4-chlorobenzophenone (PhOC-C$_6$H$_4$-Cl) | styrene | 0.5 | 91 |
| 23 | 4-chloroanisole (MeO-C$_6$H$_4$-Cl) | n-butyl acrylate (CH$_2$=CH-C(O)-OnBu) | 1 | 85 |
| 24 | 4-chloroanisole (MeO-C$_6$H$_4$-Cl) | styrene | 1 | 80 |
| 25 | 4-chlorotoluene (Me-C$_6$H$_4$-Cl) | styrene | 0.5 | 92 |
| 26 | 4-chlorobenzyl alcohol (HOH$_2$C-C$_6$H$_4$-Cl) | styrene | 0.5 | 90 |

[a]Chloroarene (1 mmol), olefin (1.2 mmol) LDH-Pd⁰ (3 mol %), [NBu$_4$]Br (10 mmol), and tri-n-butyl amine (1.2 mmol). Microwave power 400 W and temperature 130° C.

EXAMPLES 27–32

In an effort to compare the reactivity of LDH-Pd⁰ with other heterogeneous catalysts namely Pd/C, Pd/SiO$_2$, resin-Pd⁰ and Pd/Al$_2$O$_3$ in the Heck-olefination, separate experiments were conducted under identical conditions with the same ingredients and the results are summarized in Table 3. The activity of various catalysts in the Heck-olefination of 4chloroanisole is found to be in the order: LDH-Pd⁰ >resin-Pd⁰>Pd/C>Pd/Al$_2$O$_3$>Pd/SiO$_2$. These results indicate that the basic support, LDH facilitates the oxidative addition of Pd⁰ with 4-chloroanisole and eventually the Heck-olefination reaction.

The procedure was followed as in example 9 with various catalysts between 4-chloroanisole and styrene under thermal conditions and the results are presented in Table 3.

TABLE 3

Heck-Olefination of 4-Chloroanisole with Styrene Using Various Palladium Catalysts[a]

| Example | Catalyst | Yield (%) |
|---|---|---|
| 27 | LDH-Pd⁰ | 76 |
| 28 | resin-Pd⁰ | 29 |

TABLE 3-continued

Heck-Olefination of 4-Chloroanisole with Styrene Using Various Palladium Catalysts[a]

| Example | Catalyst | Yield (%) |
|---|---|---|
| 29 | Pd/C | 28 |
| 30 | Pd/Al$_2$O$_3$ | 22 |
| 31 | Pd/SiO$_2$ | 15 |
| 32 | PdCl$_2$ | 5 |

[a] 4-chloroanisole (1 mmol), olefin (1.2 mmol), Palladium catalyst (3 mol %), [NBu$_4$]Br 3.23 g (10 mmol), and tributylamine (1.2 mmol) were stirred at 130° C. for 40 h.

2. Suzuki Coupling

Scheme 2

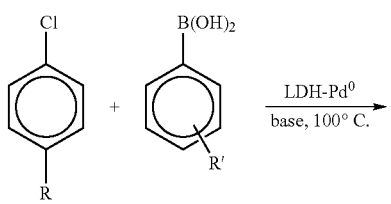

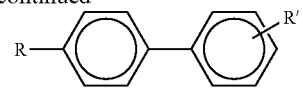

EXAMPLE 33

Suzuki Coupling Between Chlorobenzene and Phenylboronic Acid Catalysed by LDH-Pd$^0$ Chlorobenzene (1 mmol), phenylboronic acid (1.5 mmol), potassium fluoride (3 mmol), LDH-Pd$^0$ (1 mol %) and 1,4-dioxane-water (5:1, 5 mL) were charged in a round-bottomed flask. Reactions were carried out at 100° C. for 10 h. After completion of the reaction (monitored by TLC), the catalyst was filtered and the reaction mixture was poured into water and the aqueous phase was extracted with ether. After drying, the corresponding product was purified by crystallization from diethyl ether-pentane.

EXAMPLES 34–40

The procedure was followed as in example 33 and the results are given in Table 4.

TABLE 4

Suzuki Coupling Reactions of Chloroarenes with Arylboronic Acids[a]

| Example | Arylboronic acid | Haloarene | Yield (%) |
|---|---|---|---|
| 33 | C$_6$H$_5$–B(OH)$_2$ | C$_6$H$_5$–Cl | 93 (92)[b] |
| 34 | 3-NO$_2$-C$_6$H$_4$–B(OH)$_2$ | C$_6$H$_5$–Cl | 90 |
| 35 | 4-Me-C$_6$H$_4$–B(OH)$_2$ | C$_6$H$_5$–Cl | 60 |
| 36 | 2-naphthyl–B(OH)$_2$ | C$_6$H$_5$–Cl | 80 |

TABLE 4-continued

Suzuki Coupling Reactions of Chloroarenes with Arylboronic Acids[a]

| Example | Arylboronic acid | Haloarene | Yield (%) |
|---|---|---|---|
| 37 | 4-F-C6H4-B(OH)2 | C6H5-Cl | 70 |
| 38 | C6H5-B(OH)2 | 4-MeCO-C6H4-Cl | 60 |
| 39 | C6H5-B(OH)2 | 4-MeO-C6H4-Cl | 90 |
| 40 | 4-Me-C6H4-B(OH)2 | 4-MeCO-C6H4-Cl | 88 |

[a]Chloroarene (1 mmol), arylboronic acid (1.5 mmol), LDH-Pd[0] (1 mol %) and KF (3 mmol), 100° C., 10 h. All the reactions were carried out with 1,4-dioxane-water (5:1, 5 mL) as solvent.
[b]Under NAIL conditions, 8 h.

3. Sonogashira Coupling

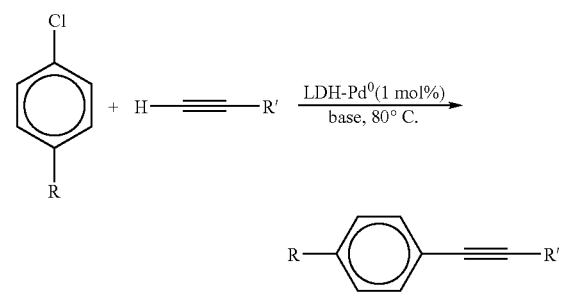

Scheme 3.

EXAMPLE 41

Sonagashira Coupling Between Chlorobenzene and Phenylacetylene Catalysed by LDH-Pd[0]

To a stirred slurry of chlorobenzene (1 mmol), cuprous iodide (7.6 mg, 0.04 mmol), and LDH-Pd[0] (1 mol %), in THF (2 mL) and water (4 mL) was added triethylamine (152 mg, 1.5 mmol). A solution of 1.25 mmol of phenylethylene in THF (2 mL) was then added over 2 h. After completion of the reaction, the solvent was evaporated, and the residue was treated with pentane. The solution was filtered to obtain the catalyst and evaporation of the solvent gives the coupling product.

EXAMPLES 42–43

The procedure was followed as in example 41 and the results are given in Table 5.

TABLE 5

Cross Coupling Reactions Between Phenylacetylene and Chloroarenes[a]

| Example | Chloroarene | Phenylacetylene | Time (h) | Yields (%) |
|---|---|---|---|---|
| 41 | C6H5-Cl | C6H5-C≡CH | 30 / 27 | 95 / 95[b] |
| 42 | 4-MeO-C6H4-Cl | C6H5-C≡CH | 48 | 60 |

TABLE 5-continued

Cross Coupling Reactions Between Phenylacetylene and Chloroarenes[a]

| Example | Chloroarene | Phenylacetylene | Time (h) | Yields (%) |
|---|---|---|---|---|
| 43 | 4-nitrochlorobenzene | phenylacetylene | 40 | 82 |

[a]Chloroarene (1 mmol), phenylacetylene (1.1 mmol), LDH-Pd[0] (1 mol %), Et$_3$N (1.5 mol), 80° C. All reactions were carried out with THF-water (1:1, 8 mL) as solvent system.
[b]Under NAIL conditions.

4. Stille Type Coupling

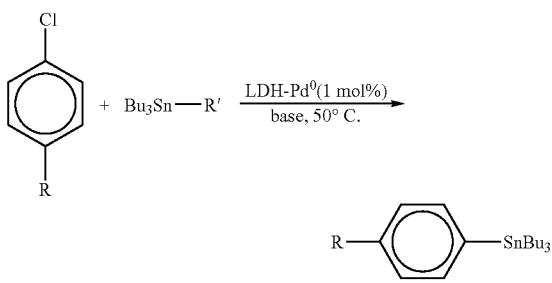

Scheme 4

EXAMPLE 44

Stille Type Couping Between Chlorobenzene and Tributyltin Reagent Catalysed by LDH-Pd[0]

A round-bottomed flask was charged with LDH-Pd[0] (1 mol %), potassium acetate (294 mg, 3 mmol), and NMP (4 ml). To this 4-chloroanisole (1 mmol) and tributyltin hydride (2 mmol) were added successively, and the mixture was stirred at 50° C. for 16 h.

The reaction mixture was diluted with benzene, washed with water and catalyst was collected for next cycle.

EXAMPLES 45–49

The procedure was followed as in example 44 and the results are given in Table 6.

TABLE 6

Stannylation of Haloarenes with LDH-Pd[0] catalyst[a]

| Example | Chloroarene | Tin reagent | Yield |
|---|---|---|---|
| 44 | chlorobenzene | Bu$_3$Sn—H | 90 (91)[b] |
| 45 | 4-chloroanisole (MeO) | Bu$_3$Sn—H | 80 |
| 46 | 4-nitrochlorobenzene (O$_2$N) | Bu$_3$Sn—H | 90 |
| 47 | chlorobenzene | Bu$_3$Sn—allyl | 80 |
| 48 | 4-chloroanisole (MeO) | Bu$_3$Sn—allyl | 65 |
| 49 | 4-nitrochlorobenzene (O$_2$N) | Bu$_3$Sn—allyl | 70 |

[a]Chloroarene (1 mmol), trialkyltin reagent (2 mmol), potassium acetate (3 mmol), LDH-Pd[0] (2 mol %). All the reactions were carried out with NMP as solvent, 50° C., 16 h.
[b]Under NAIL conditions, 12 h.

The main advantages of the present invention are:
1. A novel and ecofriendly process for the synthesis of coupling products from haloarenes that include highly unreactive chloroarenes by C—C bond formation is presented.
2. The present process dispenses the use of soluble palladium catalysts instead a heterogeneous reusable LDH-Pd (0) is used.
3. Nanopalladium catalyst, LDH-Pd(0) is prepared and used as heterogeneous catalyst for the synthesis of coupling products by C—C bond formation reactions. The use of heterogeneous nanopalladium catalyst precludes the presence of palladium in traces with the product.
4. The stereoselectivity and the yields are good.
5. The work-up procedure is simple.
6. The catalyst is subjected to many recycles, which displayed consistent activity.
7. The present process is environmentally safe since there is no disposal problem.
8. The process is economical.

We claim:

1. A process for the preparation of a reusable nanopalladium(0) catalyst, comprising:

combining a $PdCl_4^{2-}$ compound with a support to obtain a support-$PdCl_4$ composition, wherein the support is a layered double hydroxide support (LDH) or a quaternized ammonium support, wherein the quaternized ammonium support has the general formula of $S'NR_3^+ X^-$, where S' is an unmodified surface support, of resin or silica, R is methyl, ethyl, propyl, or butyl, and X is Cl, Br, I, F, OH, or OAc; and reducing the support-$PdCl_4$ composition with a reducing agent to produce the nanopalladium(0) catalyst.

2. The process of claim 1, wherein the nanopalladium(0) catalyst is LDH-$Pd^{(O)}$, wherein LDH is a class of layered material comprising alternating cationic hydroxide layers of the formula $M(II)_{l-x}M(III)_x(OH)_2^{x+}$ and anionic layers of the formula $A^{n-} \cdot zH_2O$, wherein M(ll) is $Mg^{2+}$, $Mn^{2+}$, $Fe^{2+}$, $Co^{2+}$, $Ni^{2+}$, $Cu^{2+}$, $Zn^{2+}$ or $Ca^{2+}$, wherein M(III) is $Al^{3+}$, $Cr^{3+}$, $Mn^{3+}$, $Fe^{3+}$ or $Co^{3+}$, wherein A is an interstitial anion and is nitrate, carbonate or chloride, x is 0.2 to 0.33, and Z is the number of water molecules and ranges from 1 to 4.

3. The process of claim 1, wherein the $PdCl_4^{2-}$ compound comprises $Na_2PdCl_4$.

4. The process of claim 1, wherein the nanopalladium(0) catalyst is substantially free of phosphine.

5. The process of claim 1, wherein combining the support and the $PdCl_4^{2-}$ comprises mixing the support and the $PdCl_4^{2-}$ at a temperature ranging from 200° C. to 300°C.

6. The process of claim 1, wherein combining the support and the $PdCl_4^{2-}$ comprises mixing the support and the $PdCl_4^{2-}$ for 5 hours to 24 hours.

7. The process of claim 1, further comprising separating the nanopalladium(0) catalyst from the reducing agent and washing the separated nanopalladium(0) catalyst with a solvent.

* * * * *

UNITED STATES PATENT AND TRADEMARK OFFICE
CERTIFICATE OF CORRECTION

| | |
|---|---|
| PATENT NO. | : 7,049,266 B2 |
| APPLICATION NO. | : 10/403799 |
| DATED | : May 23, 2006 |
| INVENTOR(S) | : Choudary et al. |

It is certified that error appears in the above-identified patent and that said Letters Patent is hereby corrected as shown below:

In the Claims:

Claim 5, col. 18, line 10, please delete "200°C. to 300°C." and substitute therefor --"20°C. to 30°C."--.

Signed and Sealed this

Third Day of July, 2007

JON W. DUDAS
*Director of the United States Patent and Trademark Office*